United States Patent [19]

Weitz et al.

[11] 4,233,455

[45] Nov. 11, 1980

[54] PREPARATION OF DIESTERS OF OLEFINICALLY UNSATURATED 1,2 AND/OR 1,4-DIOLS

[75] Inventors: Hans-Martin Weitz, Bad Duerkheim; Juergen Hartig, Gruenstadt; Laszlo Marosi, Ludwigshafen, all of Fed. Rep. of Germany

[73] Assignee: BASF Aktiengesellschaft, Fed. Rep. of Germany

[21] Appl. No.: 26,995

[22] Filed: Apr. 4, 1979

[30] Foreign Application Priority Data

May 11, 1978 [DE] Fed. Rep. of Germany ....... 2820519

[51] Int. Cl.[3] ........................................... C07C 67/055

[52] U.S. Cl. ................................ 560/244; 260/410.6; 252/462; 252/466 R; 252/466 PT; 252/470; 252/472; 252/473; 252/474

[58] Field of Search .............................. 560/244, 246; 260/410.6

[56] References Cited

U.S. PATENT DOCUMENTS

| | | | |
|---|---|---|---|
| 3,671,577 | 6/1972 | Ono | 560/244 |
| 4,100,361 | 7/1978 | Weitz | 560/244 |

OTHER PUBLICATIONS

Kulifay, J. Am. Chem. Soc., 83, pp. 4916–4919 (1973).

*Primary Examiner*—Joseph E. Evans
*Assistant Examiner*—Michael Shippen
*Attorney, Agent, or Firm*—Keil & Witherspoon

[57] ABSTRACT

Diesters of olefinically unsaturated 1,2- and/or 1,4-diols are prepared by reacting a conjugated diolefin, oxygen and a fatty acid, in the gas phase or liquid phase, over a solid catalyst which contains palladium and/or platinum and a further metal, which has an atomic number of from 21 to 30, from 39 to 48 or from 57 to 80, but is not a platinum metal, the catalyst having been obtained by reduction of compounds, applied to a carrier, of platinum and/or palladium and the further metal, and heating at 400° C. or above.

3 Claims, 1 Drawing Figure

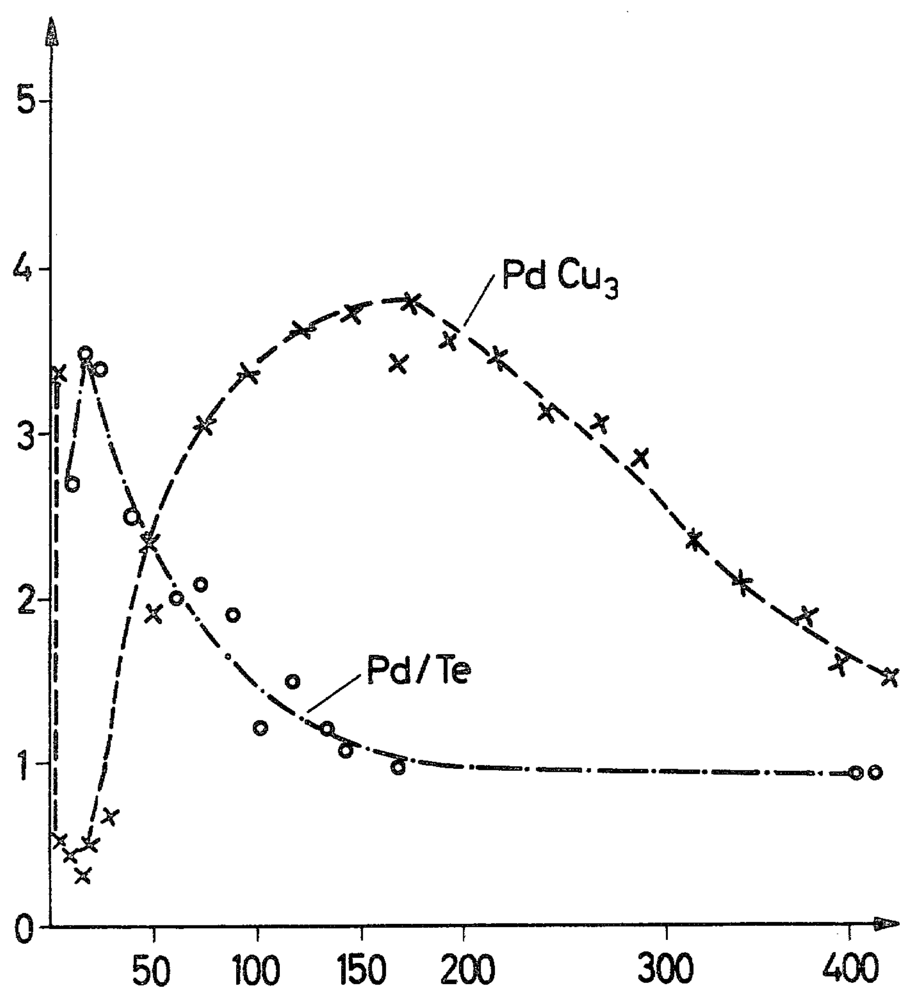
5
4
3
2
1
0
50
100
150
200
300
400
Pd Cu3
Pd/Te

PREPARATION OF DIESTERS OF OLEFINICALLY UNSATURATED 1,2 AND/OR 1,4-DIOLS

The present invention relates to a process for the preparation of diesters of olefinically unsaturated 1,2- and/or 1,4-diols, especially the preparation of butenediol diacetates, ie. but-2-ene-1,4-diol diacetate and but-1-ene-3,4-diol diacetate, by reaction of a conjugated diolefin with oxygen and a fatty acid over a solid catalyst which contains palladium or platinum and at least one element from the group of the transition metals.

German Laid-Open Application DOS No. 2,217,452 discloses that dienes, eg. butadiene, can be reacted with oxygen and carboxylic acids over solid catalysts containing palladium and, in particular, selenium or tellurium, to give unsaturated diol diacetates. It is a disadvantage of this process that the most effective catalyst combinations contain the toxicologically unsafe elements selenium and tellurium. This requires special precautionary measures during the preparation of the catalysts. Furthermore, the catalysts are slightly soluble in the very aggressive reaction mixture. Traces of the catalyst are found in the diester and may become entrained in the secondary products. Furthermore, such entrainment of catalyst constituents implies a loss of catalyst from the reaction chamber.

Other catalysts which have been described for this reaction, which is described as an acetoxylation of diolefins, contain palladium on a carrier in combination with, for example, dissolved copper salts, lithium salts and other salts, eg. antimony chloride, as the active component (cf. Japanese Patent Application Nos. 77/12,170 and 77/18,162). However, these catalysts suffer from several technical disadvantages. One or more of the catalyst constituents are dissolved in the reaction mixture, ie. they require expensive separation and recycling, and the selectivity of the process is low. The last-mentioned proposals are therefore disadvantageous even compared to the process described at the outset, and cannot be carried out on an industrial scale.

We have found that diesters of olefinically unsaturated 1,2- and/or 1,4-diols can be obtained in high yield, with high selectivity and high space-time yield, by reacting 1,3-diolefins, eg. butadiene, with oxygen and acetic acid in the liquid phase or gas phas over a solid catalyst, if the catalyst used contains, in addition to palladium or platinum, an element from the group of the transition metals (transition elements).

The transition metals are elements of atomic numbers 21–30, 39–48 and 57–80. Particularly suitable metals, for the purposes of the invention, are those of type I according to the Dehlinger classification (cf., for example, Remy, Lehrbuch der Anorg. Chemie (1973), volume II, page 39), ie. manganese, iron, cobalt, nickel, copper, silver and gold; amongst these, iron and copper are preferred. Of course, the platinum metals, ie. ruthenium, rhodium, palladium, osmium, iridium and platinum are not intended to be regarded as transition metals in the present context; mixtures of, for example, palladium and platinum are no more effective than each of these metals alone.

The catalyst is preferably a supported catalyst; suitable starting materials may be obtained by the conventional methods used for supported palladium and platinum catalysts. For example, they may be prepared by dispersing a carrier in a solution which contains a palladium or platinum compound and one or more compounds of the transition metals, evaporating the solvent and reducing the residue in a stream of gas, consisting, for example, of hydrogen or of nitrogen charged with a reducing compound, eg. hydrazine, methanol or formaldehyde. The reduction of the dried catalyst can however also be carried out with a liquid reducing agent.

The catalyst can also be prepared by treating the carrier and solution conjointly with a precipitant, for example an alkaline precipitant, and isolating and reducing the precipitate.

A very useful method of preparation of the catalyst is to precipitate the metal directly from an aqueous salt solution by means of a reducing agent, eg. formaldehyde, hydrazine and the like at a suitable pH (cf., for example, J. Amer. Chem. Soc. 83 (1961), 4,916).

Advantageously, the crude catalysts thus obtained are additionally heated at a higher temperature in a reducing gas stream.

The palladium and/or platinum and the other elements can be deposited on the carrier simultaneously or in optional sequence; in some cases, the carrier can be added in the form of a soluble compound and be coprecipitated with the active metal.

Any reduction process by which the elements used are converted to the metallic state can be employed.

Examples of suitable carriers are active charcoal, bauxite, pumice, silica gel, kieselguhr and other forms of silica, magnesia, clay, alumina and the like. At times, the suitability of the carrier can be improved by a conventional pretreatment, for example with an acid.

The particular palladium and/or platinum compound used to prepare the catalyst is not critical; for example, halogen-containing palladium and/or platinum compounds, eg. palladium chloride and the platinum chlorides, a salt of an organic acid, eg. palladium acetate or platinum acetate, or the nitrates, oxides and the like, can be used. However, other palladium or platinum compounds, in particular complex compounds, eg. hexachloroplatinic acid, sodium platinosulfate, ammonium hexachloroplatinate and others, can also serve as starting materials. The form of the compounds used to introduce the transition metals, to be employed according to the invention, into the catalysts can also be chosen substantially as desired. In general, it is advantageous to employ soluble compounds.

The amount of catalytically active metals on the carrier is usually from 0.1 to 20% by weight, though higher and lower concentrations are feasible. The decision as to the most advantageous amount may also be determined by economic considerations. In case of doubt, it can be established by exploratory experiments.

Particularly preferred and exceptionally suitable catalysts are palladium catalysts of the type described, which contain active charcoal as the carrier and, in addition to from 1 to 10% of palladium, based on total catalyst weight, from about 1 to 20% of copper and/or from 1 to 10% of iron. Higher concentrations of palladium than those stated can be used, but in general offer no particular advantage, since the space-time yield and conversion no longer increase proportionately to the metal concentration. It is essential to the invention that these elements should not be in the form of random physical mixtures but should form more or less highly ordered, inter-metallic compounds or mixed crystals. The formation of such inter-metallic phases is easily ascertainable by X-ray structural analysis.

It is known that inter-metallic phases which contain platinum or palladium have a cubic face-centered, cubic body-centered or tetragonal structure, and superlattices may also occur. These phases are known per se and are described, for example, in Gmelins Handbuch der Anorganischen Chemie, 8th edition, volume 68, part A, pages 617–652 (1951).

To accelerate the formation of intermetallic compounds or of the mixed crystals, it can be advantageous to use ternary metal systems. For example, it has been found that the formation of the $Pd_3Fe$ phase is greatly accelerated by adding small amounts of chromium (for example from 0.1 to 1% weight, based on the carrier). As a result, such catalysts can under certain circumstances be obtained at lower temperatures than when only two metals are provided for their preparation.

An essential measure in the production of catalysts in which the metals in question form intermetallic compounds or phases is the heating stage. In general, its duration, and the temperature reached, are interrelated. It has proved advantageous to heat the material for from 15 minutes to 4 hours at from 400° to 900° C., the shorter heating time in general corresponding to the higher temperature. Since, on heating, the catalytically active state, once it has been reached, ultimately becomes stabilized to some degree, it is in general not necessary to impose a certain maximum heating time. If the carrier or the metals tend to oxidize under the heating conditions, the heating is advantageously carried out in a reducing atmosphere, for example in pure hydrogen. The success of the heat treatment achieved can in each case be assessed both by determining the catalyst activity and by determining the X-ray structure.

We have found, without being able to give a specific reason, that catalysts which can be demonstrated to contain intermetallic phases or mixtures of such phases are catalytically particularly active for the purposes of the invention. Catalysts with a cubic face-centered crystal structure, such as is found, for example, in the compounds $Pd_3Fe$ and $PdCu_3$, have proved very particularly effective. However, it has been found that it is not necessary to employ the starting materials, which give these compounds, in the stoichiometric ratio. Because of the extent of these phase zones, the composition can be varied within wide limits and, depending on the conditions, the crystal lattice may exhibit superlattices or be distorted. The lattice structure of the intermetallic compounds can be determined in the presence of the carriers. Another critical factor in the catalytic activity, in addition to the formation of intermetallic phases, is the crystallite size of the active compounds. To achieve a high activity, the crystallite size should be as small as possible, for example less than 100 nm, preferably less than 50 nm and in particular less than 20 nm. The crystallite size of the metal component can be varied by suitable choice of the conditions of preparation, and can be ascertained by X-ray methods.

The reaction to be catalyzed may be carried out batchwise or continuously, by any conventional method, for example using a fixed bed, fluidized bed or three-phase moving bed, the chosen state of aggregation of the reaction mixture being a factor in the choice of method.

The reaction temperature is as a rule from 70° to 180° C. In the gas phase it is preferably from 120° to 150° C. In the liquid phase it is, for example, from 70° to 110° C. The reaction pressure is determined by the procedure used and may be from atmospheric pressure to, for example, 100 bar.

Not only 1,3-butadiene, but also other conjugated diolefins, eg. isoprene, 2,3-dimethyl-1,3-butadiene, 1,3-pentadienes and the like, are accessible to the reaction described. Instead of the pure diolefins, hydrocarbon mixtures which in addition to the diolefins contain monoolefins and paraffin hydrocarbons may be used. Suitable fatty acids, for the purpose of the invention, are formic acid, acetic acid and propionic acid. Longer-chain fatty acids are in general of less interest, since hitherto there are no special applications for their esters which could not be met by the esters of, for example, acetic acid.

The butenediol diesters obtainable by the process of the invention are valuable intermediates, for example for the preparation of butenediol and butanediol. Butene-3,4-diol diacetate (vinylglycol diacetate), formed in minor amounts, is a suitable intermediate for the preparation of vitamins and other biologically active compounds.

The 2-methyl-1,4-diacetoxy-2-butenes obtained by acetoxylation of isoprene are valuable intermediates, for example for the synthesis of terpene compounds.

If, after a certain period of operation, the activity of the catalyst declines, it can frequently be restored by suitable methods. For example, a deposit of polymeric compounds on the catalyst can be removed with the aid of suitable solvents or by careful treatment with oxygen-containing gases. If the activity of the catalyst has been impaired by oxidation phenomena, the catalyst can in many cases be regenerated by treatment with reducing agents, eg. hydrazine, formaldehyde, hydrogen, carbon monoxide, methanol (vapor) and the like.

EXAMPLE 1

8.34 g of $PdCl_2$ are dissolved in a mixture of 20 ml of 4 N hydrochloric acid, 20 ml of 30% strength nitric acid and a solution of 8.96 g of copper powder in 84 ml of 30% strength nitric acid. 100 g of active charcoal of particle size 0.4–0.8 mm, which has been washed with nitric acid, are moistened with 100 ml of water, the solution is added and the mixture is boiled. Whilst it is boiling, a solution of 70 g of hydrazine hydrochloride, 400 ml of water and 300 ml of aqueous 15% strength ammonia solution is added gradually and the mixture is stirred for a further 1.5 hours at the boil. The suspension is filtered and the residue is washed neutral with water, rinsed with 50 ml of methanol, dried for 10 hours under reduced pressure at 70° C. and treated for 30 minutes at 800° C. with hydrogen in a tubular furnace.

The structural analysis of the catalyst shows a $PdCu_3$ phase with a small amount of PdCu. The lattice constant of the $PdCu_3$ phase is 0.3696 nm and the mean crystallite size is 13 nm. The measured d-values in nm ($CuK_\alpha$ radiation source) are shown in the Table below.

TABLE

| $PdCu_3$ | (hkl) | PdCu | (hkl) |
|---|---|---|---|
| 0.37 | 001 | 0.296 | 001 |
| 0.26 | 011 | 0.209 | 011 |
| 0.213 | 111 | 0.171 | 111 |
| 0.1848 | 002 | 0.148 | 002 |
| 0.1305 | 022 | 0.1325 | 021 |

543 g of acetic acid and 25 g of catalyst are introduced into a 1 liter four-neck flask and heated to 85° C.

whilst introducing $N_2$. Butadiene and oxygen, each in an amount of 3 l/h, are introduced into the liquid for four hours with the aid of a gassing stirrer (1,000 rpm); the catalyst is then filtered off, the filtrate is freed from excess butadiene and unconverted acetic acid by distillation, and the liquid residue is analyzed. It has the following composition:

74.7% by weight of trans-1,4-diacetoxy-2-butene
11.1% by weight of cis-1,4-diacetoxy-2-butene
10.2% by weight of 3,4-diacetoxy-1-butene
0.6% by weight of trans-1-hydroxy-4-acetoxy-2-butene
1.5% by weight of cis-1-hydroxy-4-acetoxy-2-butene
1.5% by weight of 3,4-dihydroxy-1-butene monoacetate
0.3% by weight of butenyl acetates
0.2% by weight of butadienyl acetate The yield of butenediol derivatives, ie. of useful products, is accordingly more than 98.2%.

COMPARATIVE EXPERIMENT 1

The catalyst was prepared by precipitating palladium and copper on the charcoal by reduction with hydrazine, and was used immediately after drying, ie. without heating. The yield of useful product is in this case less than 0.1 g. The X-ray diagram of the catalyst shows broadened lines, without a discernible structure.

EXAMPLE 2

4.48 g of Cu powder (70.5 mg-equivalents), dissolved in 42 $cm^3$ of 33% strength $HNO_3$, are added, at room temperature, to 5.31 g of $Pd(CH_3COO)_2$ (23.7 millimoles), dissolved in 75 $cm^3$ of 50% strength ethanol.

The combined metal salt solution is added to 50 g of active charcoal which has beforehand been washed with nitric acid, and the mixture is concentrated to dryness on a rotary evaporator at 85° C. under reduced pressure from a waterpump.

The catalyst is dried for 2 hours at 150° C. in a drying oven under reduced pressure, and then for 2 hours at 150° C. in a tubular oven under a stream of nitrogen. It is then activated for 6 hours at 200° C., followed by 6 hours at 400° C., with nitrogen which has been saturated with methanol at room temperature, and is finally activated for 0.5 hour with hydrogen (20 l/h) at 800° C. The catalyst is then allowed to cool to room temperature under a stream of nitrogen.

Using the method described in Example 1, butadiene, acetic acid and oxygen are reacted over the catalyst thus prepared. The yield of butenediol diacetates was found to be 98.5%.

EXAMPLE 3

8.3 g of palladium chloride (corresponding to 5 g of Pd) and 3.6 g of iron(II) chloride ($FeCl_2.4H_2O$) (corresponding to 1 g of Fe) are separately each dissolved in 200 ml of 6 N HCl at 80° C., the combined solutions are added to 100 g of active charcoal, as described in Example 1, and the mixture is evaporated to dryness in a rotary evaporator. The residue is dried for 2 hours at 150° C. under reduced pressure and is then activated for 30 minutes under a stream of hydrogen in a tubular oven at 750° C.

The X-ray structure indicates a $Pd_3Fe$ phase with a lattice constant of 0.3845 nm; the mean crystallite size is 20 nm.

543 g of acetic acid, and the catalyst obtained as described above, are heated at 85° C. in a 1 liter flask under nitrogen, and butadiene gas and oxygen, each in an amount of 3 l/h, are introduced by means of a hollow-shaft stirrer; the experiment lasts 4 hours, after which the material is worked up as described in Example 1. 30.8 g of distillation residue are obtained, having the following composition:

66.1% by weight of trans-1,4-diacetoxy-2-butene
17.6% by weight of cis-1,4-diacetoxy-2-butene
13.0% by weight of 3,4-diacetoxy-1-butene
0.2% by weight of trans-1-hydroxy-4-acetoxy-2-butene
0.6% by weight of cis-1-hydroxy-4-acetoxy-2-butene
2.2% by weight of 3,4-dihydroxy-1-butene monoacetate
0.1% by weight of butenyl acetates (sum)
0.2% by weight of butadienyl acetate Accordingly, the yield of useful products is 99.2%.

EXAMPLE 4

A catalyst which was prepared as described in Example 1, contained 5% by weight of palladium and 1% by weight of nickel, based on total catalyst weight, and had been activated for 15 minutes at 900° C. in a stream of hydrogen, gave (under the same conditions as in Example 1) 20.2 g of useful products, the selectivity being 95.1%. The lattice constant of what was regarded as the catalytically active metal component was found to be 0.3811 nm and the crystallite size was 10.5 nm.

COMPARATIVE EXPERIMENT 4

A catalyst which had the same composition but had been treated at 400° C. in a stream of methanol/nitrogen, proved virtually inactive; only 0.9 g of useful product was obtained.

EXAMPLE 5

An experiment corresponding to Example 3, with a Pd/Co catalyst, gave 21.1 g of useful product, the selectivity being 93.3% (lattice constant of the metal phase: 0.3828 nm, mean crystallite size: 14 nm). A comparative experiment in which activation was carried out at 400° C. in a stream of methanol/$N_2$ gave only 2.0 g of useful product.

EXAMPLE 6

A vertical tubular reactor (30 mm diameter, 680 mm length) provided with a double jacket is filled with a Pd/Cu catalyst which has been prepared as described in Example 1, and has been activated, and is heated to 90° C. by circulating oil through the jacket. At the upper end of the tube, 200 ml of acetic acid, 3 l (S.T.P.) of butadiene gas and 3 l (S.T.P.) of oxygen are introduced per hour, the pressure being 1 bar.

The liquid reaction product obtained at the bottom end is collected, examined for useful products by means of quantitative GC analysis, and worked up by distillation. The variation with time of the content of useful products (=sum of the butenediol diacetates) in the material discharged is shown in the accompanying drawing in which the total of useful products in percent by weight is plotted against time in hours. The content of butenediol compounds in the reaction mixture after the start-up phase is at most 3.5% by weight. The palladium content in the reaction mixture obtained is 3 ppm and the copper content 21 ppm.

After operating for 400 hours, the catalyst activity had decreased to a point where regeneration was attempted. This was achieved by drying the catalyst and treating it with methanol-laden nitrogen for 4 hours at 200° C. and then for 4 hours at 400° C. After restarting the experiment, the content of useful products in the reaction mixture was found to be 4.5% by weight.

COMPARATIVE EXPERIMENT 6

The reactor described in Example 6 is filled with 250 ml of a Pd/Te catalyst which has been prepared as described in Example 13 of German Laid-Open Application DOS No. 2,217,452, and is operated as described above. The Figure again shows the concentration of useful products as a function of the time of operation.

EXAMPLE 7

600 parts of glacial acetic acid and 15 parts of a catalyst, containing palladium and copper and prepared as described in Example 1, are heated at 95° C. in a 1 liter three-neck flask provided with an Anschütz attachment, dropping funnel, gassing stirrer, internal thermometer, gas inlet tube and reflux condenser surmounted by a solid carbon dioxide condenser, the apparatus having first been flushed with nitrogen. Progressively, over 4 hours, 12,000 parts by volume of oxygen are introduced and 36.5 parts by weight of isoprene are added. After all has been added, nitrogen is passed through the reaction mixture at 95° C. for 30 minutes, the mixture is allowed to cool and the catalyst is filtered off. The filtrate (592.8 parts) contains, according to gas-chromatographic analysis, 5.8% by weight of 2-methyl-1,4-diacetoxy-2-butene (28% cis, 72% trans).

EXAMPLE 8

600 parts of glacial acetic acid and 15 parts of a catalyst containing palladium and copper (5% of Pd, 19.2% of Cu) (carrier: Desorex K, 0.4–0.8 mm) are heated at 95° C. in a 1 liter three-neck flask provided with an Anschütz attachment, dropping funnel, gassing stirrer, internal thermometer, gas inlet tube and reflux condenser surmounted by a solid carbon dioxide condenser, the apparatus having first been flushed with nitrogen. Over 4 hours, 12,000 parts by volume of oxygen are introduced and at the same time 36.5 parts by weight of piperylene are added dropwise. After all has been added, nitrogen is passed through the reaction mixture at 95° C. for 30 minutes, the mixture is allowed to cool and the catalyst is filtered off. According to gas-chromatographic analysis, the filtrate (561 parts) contains 2.44% by weight of 1,4-diacetoxy-2-pentene.

EXAMPLE 9

Per hour, 200 ml of acetic acid are evaporated and passed, together with 10 l of oxygen and 10 l of 1,3-butadiene, through a reaction tube which is packed with 100 g of the Pd/Cu catalyst of Example 2 and is heated to 140° C. The constituents of the issuing vapors which boil above room temperature are condensed, and the acetic acid is distilled from the condensate. The residue left contains the isomeric butenediol diacetates in a weight ratio of (trans-1,2):(cis-1,2):(-3,4) of 7:1:2.

We claim:

1. A process for the preparation of diesters of olefinically unsaturated 1,2- and/or 1,4-diols by reacting a diolefin selected from the group consisting of 1,3-butadiene, isoprene, 2,3-dimethyl-1,3-butadiene and a 1,3-pentadiene with oxygen and a fatty acid in the gas phase or liquid phase over a solid catalyst which contains palladium and/or platinum and copper in a reduced form on a solid carrier, said catalyst having been obtained by the reduction of compounds, applied to a carrier, of platinum and/or palladium and of copper, and heating at 400° C. or above.

2. A process as claimed in claim 1, wherein the platinum and/or palladium and copper form an intermetallic compound, detectable by X-ray structural analysis, in the catalyst.

3. A process as claimed in claim 1, wherein butadiene is used as the diolefin and acetic acid as the fatty acid.

* * * * *